United States Patent [19]

Berner et al.

[11] Patent Number: 5,987,396

[45] Date of Patent: *Nov. 16, 1999

[54] COMPUTER-CONTROLLED DEVICE FOR DETECTING OPTICAL TRANSMISSION AND/OR REMITTANCE PROPERTIES OF A MEASURING OBJECT, METHOD FOR OPERATING SUCH A DEVICE AND METHOD FOR INITIALIZING MEASURING FUNCTIONS OF SUCH A DEVICE

[75] Inventors: Markus Berner, Niederhasli; Thomas Senn, Dielsdorf, both of Switzerland

[73] Assignee: Gretag Aktiengesellschaft, Switzerland

[*] Notice: This patent issued on a continued prosecution application filed under 37 CFR 1.53(d), and is subject to the twenty year patent term provisions of 35 U.S.C. 154(a)(2).

[21] Appl. No.: 08/517,678

[22] Filed: Aug. 22, 1995

[30] Foreign Application Priority Data

Aug. 24, 1994 [EP] European Pat. Off. ............. 94810485

[51] Int. Cl.$^6$ .................................................. G01N 21/17
[52] U.S. Cl. .............................................. 702/172; 380/4
[58] Field of Search ............................. 364/468.01, 525, 364/550, 571.01; 386/3.4, 9.23, 25, 48, 50; 702/137, 127, 40, 172, 159; 356/432

[56] References Cited

U.S. PATENT DOCUMENTS

| 4,242,730 | 12/1980 | Golias et al. ............................ 356/39 |
| 4,740,890 | 4/1988 | William ................................... 364/200 |
| 4,937,764 | 6/1990 | Komatsu et al. ....................... 356/432 |
| 5,214,697 | 5/1993 | Saito ......................................... 380/4 |

FOREIGN PATENT DOCUMENTS

| 0 603 448A1 | 6/1994 | European Pat. Off. . |
| WO85/02310 | 5/1985 | WIPO . |

OTHER PUBLICATIONS

IBM Technical Disclosure Bulletin, "Method for Creating Many Individually–Distributable Programs On a Single Diskette", S.R. White, vol. 27, No. 7A, Dec. 1984, pp. 3903–3904.

Catalyst Semiconductor DataBook 92/93, CAT35C704/CAT35C7041 4K–Bit Secure Access Serial E$^2$ PROM, 1992 by Catalyst Semiconductor, Inc., title page and pp. 6–14 through 6–27.

Handbuch für Hardlock E–Y–E, Fast Electronic GmbH, Version 2.1, Dec. 1, 1989, Munchen, Germany, pp. 2–1 through 2–7.

Primary Examiner—William Grant
Assistant Examiner—Steven R. Garland
Attorney, Agent, or Firm—Burns, Doane, Swecker & Mathis, L.L.P.

[57] ABSTRACT

A computer-controlled device for detecting optical transmission and/or remittance properties of a measuring object has a measuring unit for illuminating the measuring object and for receiving the light transmitted by the measuring object and/or reflected from the measuring object. Furthermore, it has an input unit for selecting the type of measurement and the like, as well as a display unit for displaying the values measured. Moreover, it comprises a first non-volatile memory in which the measuring functions of the device are stored, as well as a control unit for controlling all procedures in the device. In a second non-volatile memory are stored release codes assigned to the individual measuring functions and, with the help of which, the control unit accesses the measuring functions in the first non-volatile memory.

21 Claims, 6 Drawing Sheets

COMPUTER-CONTROLLED DEVICE FOR DETECTING OPTICAL TRANSMISSION AND/OR REMITTANCE PROPERTIES OF A MEASURING OBJECT, METHOD FOR OPERATING SUCH A DEVICE AND METHOD FOR INITIALIZING MEASURING FUNCTIONS OF SUCH A DEVICE

This invention relates to a computer-controlled device for detecting optical transmission and/or remittance properties of a measuring object, to a method for operating such a device and to a method for initializing measuring functions of such a device according to the respective independent patent claim.

BACKGROUND OF THE INVENTION

Computer-controlled devices for detecting optical transmission and/or remittance properties of a measuring object such as densitometers or spectrophotometers are widely known. They can either be installed in fixed manner in a pressure contrivance or designed as mobile hand-held devices. Such a hand-held device in the form of a hand-held densitome meter is known from European Patent EP-A-0, 603,448. This hand-held densitometer comprises a measuring unit for receiving the light transmitted by the measuring object (e.g., a printed sheet) and/or remitted from the measuring object. Furthermore, an exemplary hand-held device described therein has an input unit that is designed as a handwheel. With the help of this handwheel, for example, the type of measurement can be input (density measurement, tonal value determination, etc.), specific parameters of the measurement can be input, the measurement can be triggered, and so forth. In the case of other hand-held devices of this type, it is also common to input such features and/or to trigger the measurement with the help of a keyboard provided on the ha hand-held device naturally comprises a display unit (e.g., an LCD display) for displaying the values measured and, as before, for displaying the selected type of measurement, the parameters, etc.

On the inside, such devices typically also have a non-volatile memory (e.g., a ROM) in which the individual measuring functions of the device are stored. These measuring functions stored in the non-volatile memory are accessed during operation of the device in such a way that all measuring functions stored in this non-volatile memory are available to the user. At the same time, a control unit (control computer, microcomputer) controls the sequence of all procedures in the device.

In principal, such devices can be equipped with a large number of measuring functions, such as density measurement, measurement of density differences, measurement of density increases, determination of pressure characteristics, determination of area coverage, contrast measurement, measurement of color shading errors, and many more measuring functions. However, the various users of such devices do not always need all of these measuring functions. Thus, when purchasing such devices, the users do not insist on the device having the unnecessary measuring functions, since in the first place, the better-equipped devices usually cost more, and secondly, the not so well-equipped devices are naturally easier to handle, since certain measuring functions are not offered as options at all and therefore cannot contribute to the user's confusion. For example, a typical printer needs the measuring functions of density, density increase and area coverage. A printing-system with high quality requirements, for example, needs the measuring functions of density, density increase, area coverage, pressure characteristic and area coverage. A processing establishment (such as a photographic film processing establishment), on the other hand, typically needs the measuring functions of density and density increase, for example. However, other users only need the measuring function of density. Still other customers do not yet know, when purchasing such a device, exactly what they will want to measure in the future, or due to a change in operation (e.g., higher quality requirements of a printing-system), additional values must suddenly be measured with such a device.

For this reason, different devices are obtainable that are equipped with various measuring functions. This is usually realized in such a way that at any given time, all the measuring functions (programs) that the device can execute are stored in the non-volatile memory (e.g., ROM). In the case of devices that can execute different measuring functions, different measuring functions (programs) are also stored in the ROM at any given time. In principle, this is a solution as to how devices with different measuring functions can be provided, while the unwanted measuring functions are not provided and thus cannot contribute to the user's confusion. However, this is disadvantageous in the production of the devices insofar as the ROMs for the devices must in each case be specifically programmed in such a way that only very specific measuring functions (programs) are stored in them. As a result, depending on the customer's wishes and/or depending on the type of device offered for sale, a special ROM must be programmed and produced, and thus the production of the various devices is relatively expensive.

SUMMARY OF THE INVENTION

A technical problem addressed by the invention is therefore to substantially simplify the production of such devices. Moreover, the invention is directed to producing the devices and their operating procedures in such a way that the devices can be easily upgraded, i.e., further measuring functions can be provided easily when the user so wishes, and without having to purchase a new device for this purpose. In this connection, it is particularly desirable for the upgrading of the device to be possible in very easy manner without, for example, having to send the device back to the manufacturer for lengthy periods.

With respect to exemplary embodiments of a device according to the present invention, this problem is solved in that stored in a second non-volatile memory are release codes assigned to the individual measuring functions, and with the help of these codes a control unit accesses the measuring functions in the first non-volatile memory. In this way, devices can be produced for which only one type of non-volatile memory (e.g., ROM) is produced, in which are stored all measuring functions (programs) that are at all possible with the device. Release codes are stored in a second non-volatile memory. The control unit can call up these release codes from the second memory and access by means of these release codes, selected measuring functions from the first non-volatile memory. Outwardly, this is expressed to the user as though only the measuring functions he desires were present in the device. Other measuring functions are not represented at all on the display unit of the device, because without the release code for these measuring functions, the measuring functions cannot be accessed at all. The measuring functions that cannot be accessed thus cannot contribute to the user's confusion. Indeed, this results in an enormous simplification for the production of the device.

Namely, it is henceforth only necessary to produce ROMs in which all measuring functions (programs) are stored. The release codes, which are very short and easy to store, determine which measuring functions (programs) can actually be accessed (i.e., practically which measuring functions the device has for the user). This makes it possible to produce the devices more easily, but moreover, it also makes it possible to upgrade these devices more easily without having to purchase a new device or having to send the device in to the manufacturer for lengthy periods, as will be explained later.

As regards an operating procedure of such a device, the technical problem described above is addressed in that by means of the control unit, one can call up from a second non-volatile memory release codes with the help of which the measuring functions stored in the first non-volatile memory are accessed by means of the control unit during operation of the device. This method makes it possible, on the one hand, to easily initialize the measuring functions of a measuring device, but moreover, it also makes it possible to subsequently upgrade a hand-held device already sold to a user, i.e., to equip it with further or other measuring functions without having to send the device to the manufacturer for lengthy periods for this purpose. Namely, only a necessary initialization code needs to be fed (i.e., supplied) to the device so that the second non-volatile memory can be unlocked to store the necessary release codes.

BRIEF DESCRIPTION OF THE DRAWINGS

Further advantageous embodiments of a device as well as further advantageous variants of an operating method and an initialization method will be better understood from a reading of the following detailed description of preferred embodiments and the accompanying drawings, wherein.

DETAILED DESCRIPTION OF PREFERRED EMBODIMENTS

Figure 1:
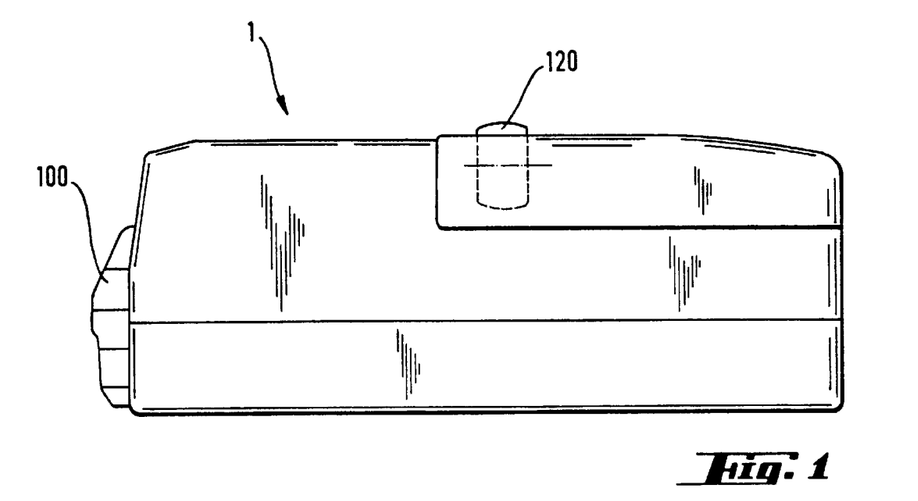
FIG. 1 shows a view of an exemplary embodiment of a device according to the invention, with the exemplary FIG. 1 embodiment being illustrated as a hand-held device.
Figure 2:
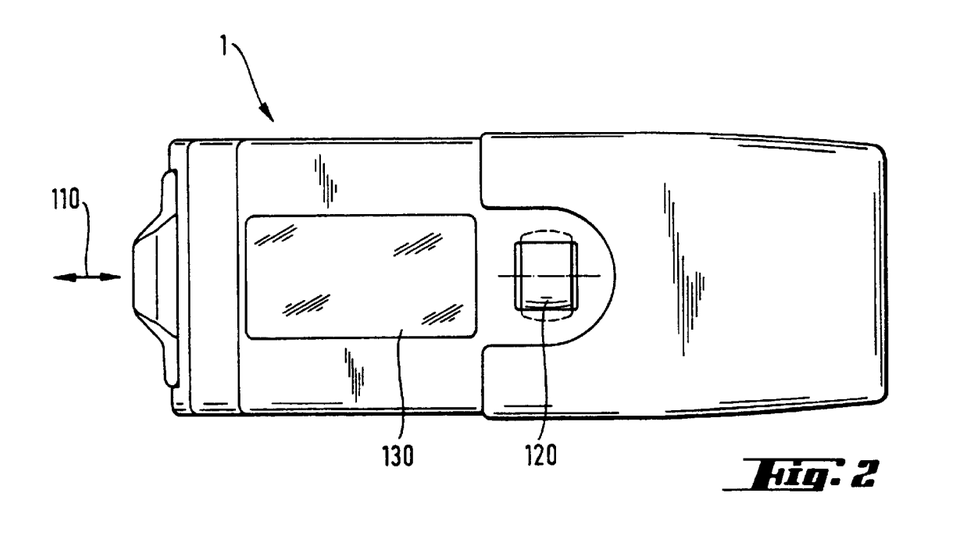
FIG. 2 shows a top view of the exemplary device of FIG. 1.

An exemplary embodiment of a device 1 according to the invention is illustrated as a handheld device 1 in FIG. 1 (side view) and FIG. 2 (top view). One recognizes a measuring unit in the form of a measuring head 100 which, to execute a measurement in the direction of the arrow 110, is extendable from and reinsertable into the device 1. In the extended state, a measuring object (not shown), e.g., a printed sheet, is illuminated by a light source provided in the measuring head 100 and the light remitted from the printed sheet is received in the measuring head 100 and subsequently analyzed. The type of measurement (e.g., density measurement), the selection of individual parameters of the measurement, and/or the triggering of the measuring procedure (extension of the measuring head, etc.) can take place with the help of a handwheel 120 as an input unit and in each case can be displayed on a display unit, e.g, an LCD display 130 (FIG. 2). With other known devices, these inputs can also take place by means of, for example, a keyboard. The values measured (e.g., densities) are displayed on the LCD display 130 after the measurement. Thus far, the hand-held device according to the invention corresponds to the state of the art as it is described, for example, in EP-A-0,603,448 mentioned in the beginning.

Figure 3:
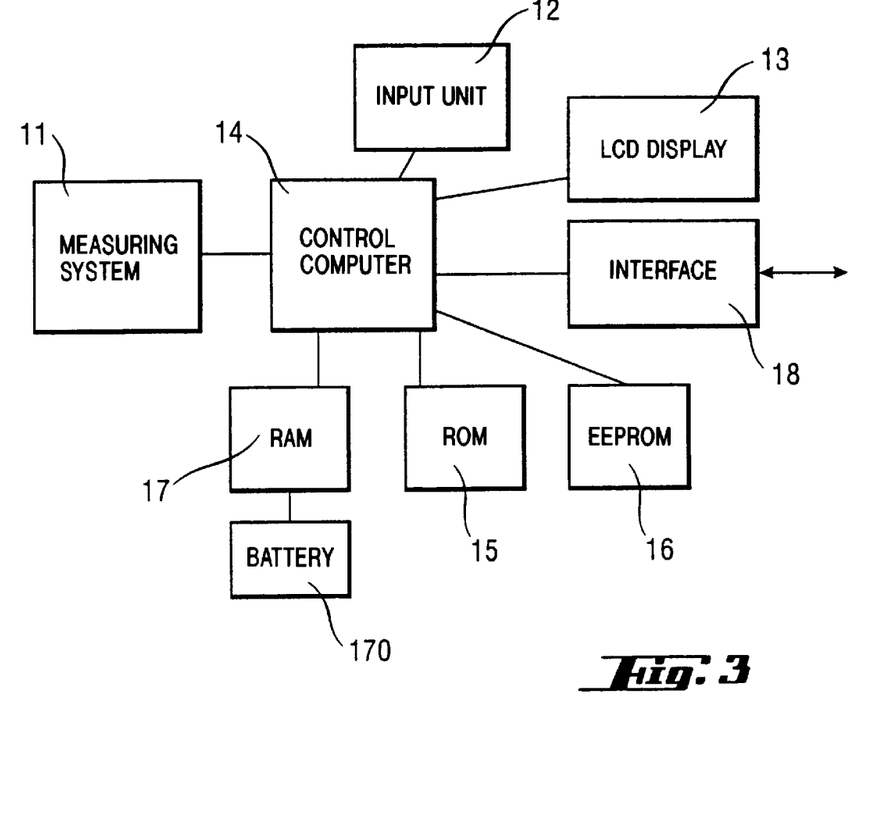
FIG. 3 shows the exemplary device of FIG. 1 in greater detail.

In such a device, the individual measuring functions are typically stored as programs in a first non-volatile memory 15, e.g., in a ROM (Read Only Memory), as is illustrated in the FIG. 3 block diagram, which shows the FIG. 1 device 1 according to an exemplary embodiment of the present invention in greater detail. In an exemplary process, a control unit in the form of a control computer 14 controls all sequences in the device. Moreover, the device comprises an input unit 12 that is, in an exemplary embodiment, implemented as the handwheel 120 shown in FIG. 1 and FIG. 2. As already mentioned, this input unit 12 can also be implemented as any other type of user controlled device, such as a keyboard. Moreover, as shown in FIG. 3, the device comprises a measuring system 10 that can correspond to any state of the art measuring system and can, in an exemplary embodiment, be produced as a measuring head 100 (FIG. 1, FIG. 2). In addition to the ROM 15, the device also comprises a second non-volatile memory 16, e.g., an EEPROM (Electrically Erasable Programmable ROM), a volatile memory 17, e.g., a RAM (Random Access Memory) buffered by means of a battery 170, a display 13 (which corresponds to display 130 of FIG. 2) as well as an interface 18 for communication with external devices.

Figure 4:
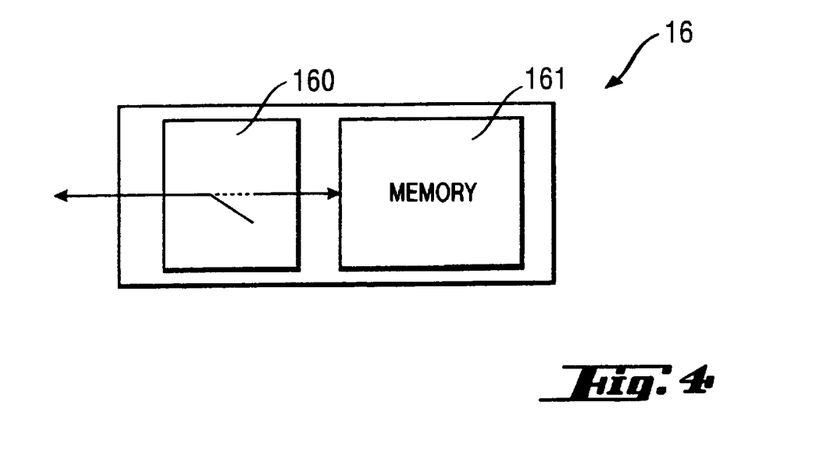
FIG. 4 shows an exemplary embodiment of a second non-volatile memory of the exemplary FIG. 1 device.

An exemplary embodiment of the EEPROM 16 (second non-volatile memory) is shown in FIG. 4 in a block diagram. The EEPROM 16 comprises a lock 161 and a non-volatile programmable memory 161. In exemplary embodiments, the lock can be any means for inhibiting access to the memory 161 by the control unit 14 (e.g., coded access). To be able to access the memory 160, the lock 150 must first be opened each time by means of, for example, a matching key (e.g., a matching code). This key is preferably unique (that is, different) for each individual device for security reasons.

The functioning of such a device in accordance with an exemplary embodiment is as follows. In principle, all measuring functions that are fundamentally executable with the device are stored in the ROM 15 in the form of programs. In the EEPROM 16, however, depending on what measuring functions the device should actually be able to execute, certain release codes (e.g., codes which release access to one or more measuring functions stored in the ROM 15 to the control unit 14) are stored which are necessary to be able to access the individual measuring functions in the ROM 15. In other words, the measuring functions in the ROM 15 are managed in such a way that they can only be accessed by means of the corresponding release codes. In principle, these release codes can be called up every time a measuring function is to be executed, the release codes being called up from the EEPROM 16 via the control computer 14. However, the release codes can also be copied to the volatile memory 17, which is battery-buffered by means of the battery 170. The release codes can thus remain preserved in the RAM 17. This has the advantage that when the device is switched on, the lock 160 of the EEPROM 16 does not have to be opened every time, in such a way that it becomes accordingly difficult to find out the key for opening the lock 160 and to read-out the EEPROM 16 without authorization and/or to copy or modify the EEPROM 16. A RAM, such as the RAM 17, can only be manipulated with great difficulty, which is why no special protective measures are provided for the RAM in accordance with exemplary embodiments. However, such protection can be provided if desired.

Figure 5:
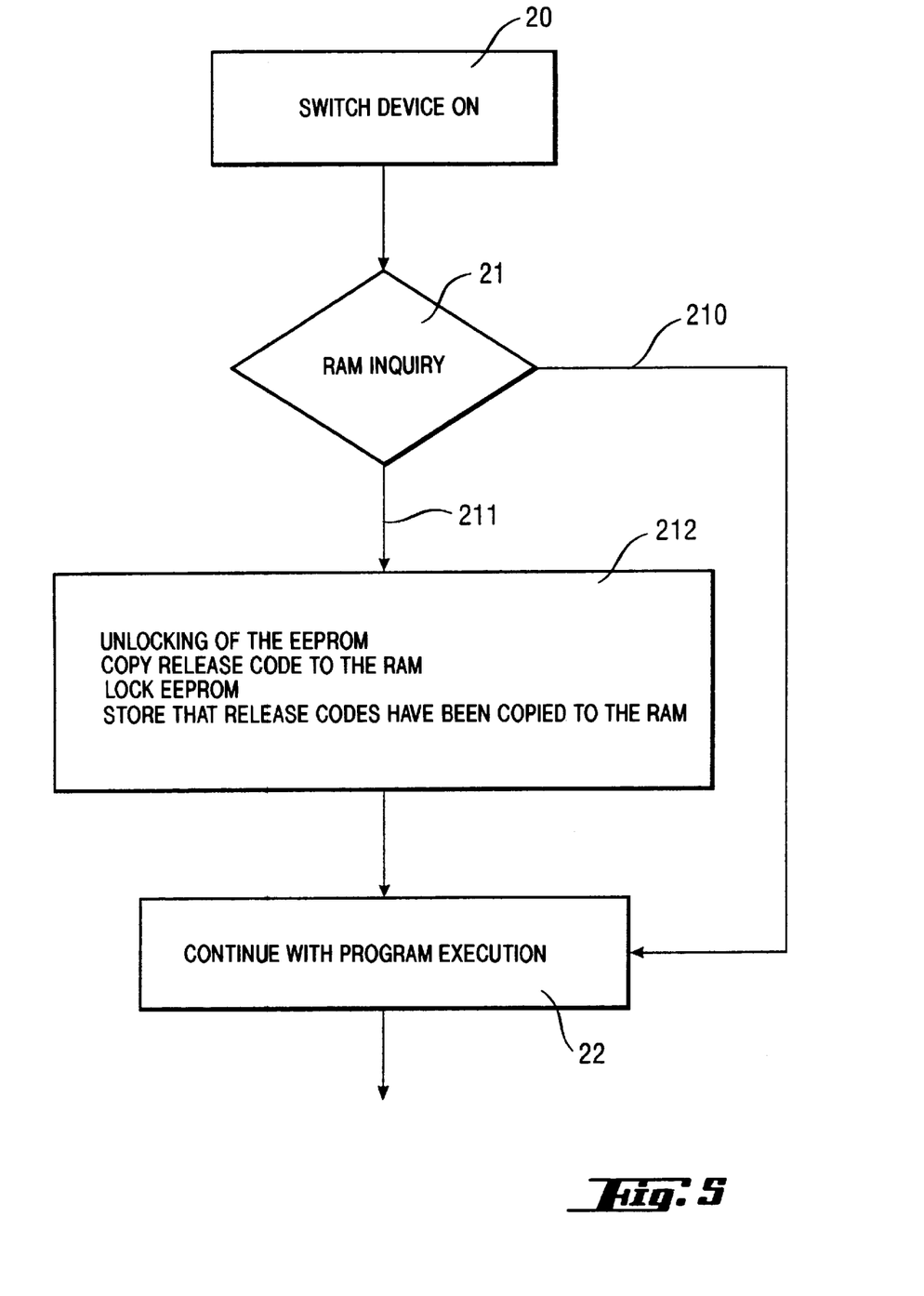
FIG. 5 shows an exemplary flow chart to elucidate steps of an exemplary process for switching on the device.

FIG. 5 illustrates how the procedures of an exemplary embodiment run when the device is switched on. In a first step 20, the device is switched on. In the next step 21, a RAM inquiry takes place; namely, it is first determined whether release codes are already stored in the RAM 17, and secondly whether a checksum, calculated and stored when the device is switched off, is correct. If no release codes are stored in the RAM 17, either the device is being switched on for the first time or the release codes have been deleted from the RAM 17. This can occur when, for example, the EEPROM is replaced. For example, when the EEPROM 16 is to be replaced, its EEPROM memory 161 (FIG. 4) can be unlocked according to step 212 by means of the key stored, for example, in the ROM 15. The contents of the EEPROM 16, in particular the release codes stored in the memory 161 of the EEPROM, are then copied to the RAM 17 after the EEPROM has been replaced. The lock 160 of the EEPROM 16 is then locked again. Information is then stored in the RAM 17 to indicate that release codes have been copied to the RAM. Only then is further program execution at step 22 continued, because only then is the device in a state of readiness.

In accordance with exemplary embodiments, the same sequence of steps also takes place, even when it is not the first time the device is being switched on, to detect whether a checksum stored in the RAM 17, is incorrect with respect to the release codes that are stored in the RAM 17. When incorrect, this means that changes have arisen in the RAM 17 that are attributable either to manipulations or to other causes. In any case, the same sequence of steps takes place as described in the preceding paragraph to store the release code of the EEPROM into the RAM 17. These two cases are represented by the path 211 and the step 212 in FIG. 5.

If release codes are stored in the RAM 17 and the checksum stored in the RAM 17 is correct, the lock 160 (e.g., coded access) of the EEPROM 16 does not need to be unlocked and the contents of its memory 161 do not need to be copied to the RAM 17, either. This is the normal case that is represented in FIG. 5 by the path 210. In this normal case, the key to open the lock 160 of the EEPROM 16 thus does not need to be called up from the ROM 15, either. Thus, in the normal case, it becomes very difficult to determine the key needed to read-out. It is therefore very difficult to copy or manipulate the EEPROM 16. However, even if someone still finds out the key for the EEPROM 16 without authorization, the key, in exemplary embodiments, is only used for a single device, since preferably a different, unique key is stored in the ROM 15 of each device.

After taking the path 210 and/or taking the path 211 of FIG. 5 and carrying out the step 212, further program execution 22 is continued and, for example, the main menu is displayed on the FIG. 3 display unit 13.

In principle, it is possible to store, in the memory 161 of the EEPROM 16, release codes by means of which the control unit 14 can access all measuring functions in the ROM 15. It is also possible, however, to store codes by means of which individual groups of measuring functions or only individual measuring functions in the ROM 15 can be accessed.

Figure 6:
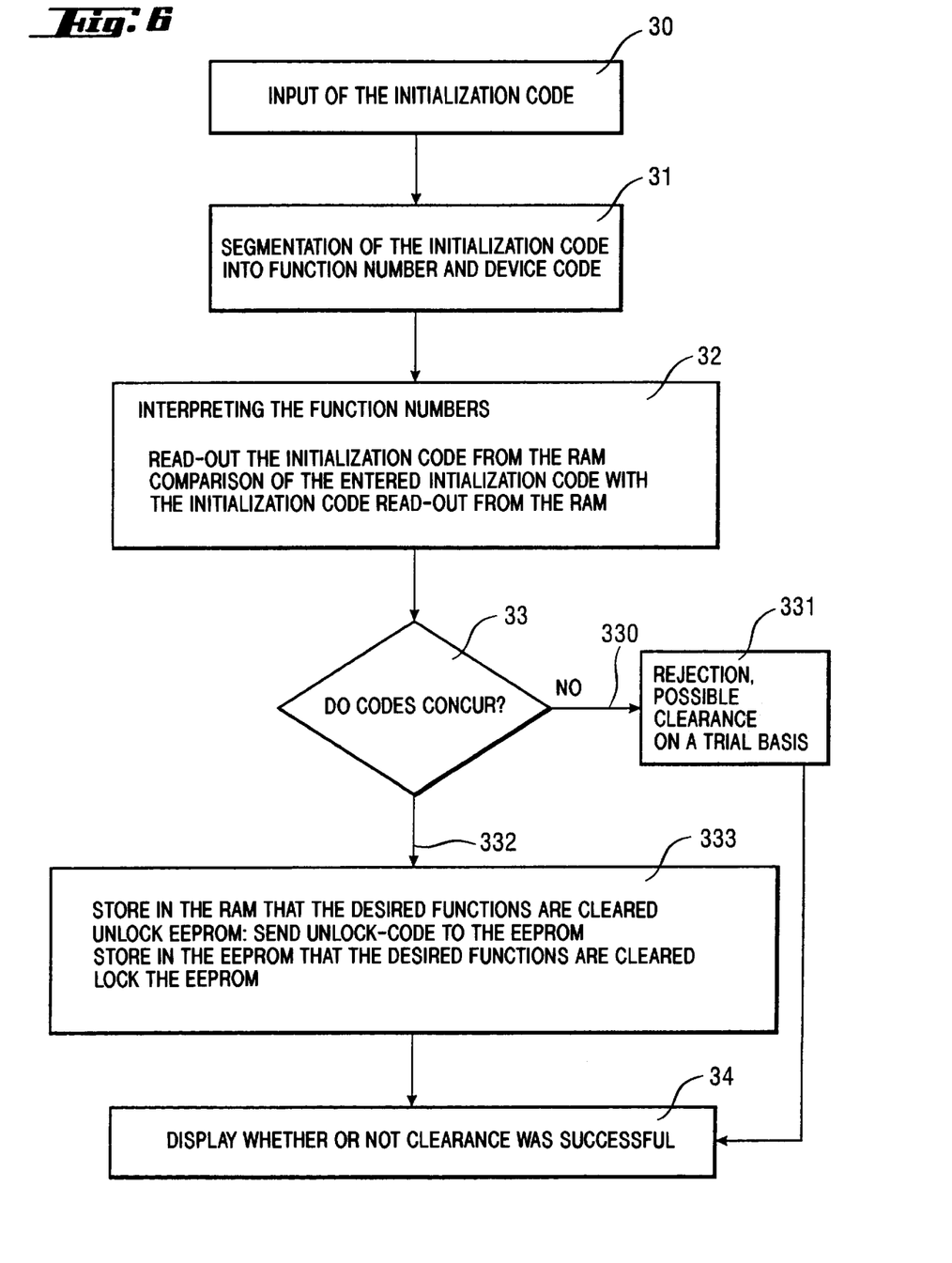
FIG. 6 shows an exemplary flow chart to elucidate steps of an exemplary process for initializing the device.

With the help of the flow chart in FIG. 6, it becomes very clear which steps, in principle, are run through when a device is upgraded in accordance with an exemplary embodiment of the invention. At first, an initialization code is input by means of the input unit 12 (e.g., by means of the FIG. 1 handwheel 120 or by means of a keyboard) in a first step 30. As an exemplary alternative, the initialization code can also be fed via the FIG. 3 interface 18 from an external computer, as will be explained later. This initialization code is segmented in a subsequent step 31 into a function number and a device code that is different for each device. In the next step 32, the function number is interpreted; in other words, it is determined which release code or, respectively, which release codes are present in the initialization code for which functions. Furthermore, the corresponding initialization code is then read from the FIG. 3 RAM 17. Namely, the contents of the initialization codes for all measuring functions executable with the device are also stored in the buffered RAM 17. The initialization code fed in is then compared with the initialization codes stored in the RAM 17.

Then, in a further step 33, it is determined whether the initialization code fed in concurs with the initialization code stored in the FIG. 3 RAM 17. If this is the case, the path 332 is taken. Then, in a further step 333, a release code is stored in the RAM 17, by means of which it is possible via the control unit 14 to access the additionally desired measuring functions in the ROM 15, i.e., the additionally desired measuring functions are "cleared". Then, the lock 160 of the EEPROM 16 is unlocked, in that the key ("unlock codeb) is sent from ROM 15 to the lock of the EEPROM 16. Then, a release code is also stored in the EEPROM 16, by means of which it is possible to access via the control unit 14 the additionally desired measuring functions in the ROM 15; in other words, it is stored in the EEPROM 16 that the additionally desired measuring functions have "cleared" such that the device 1 can be used to implement these desired functions. Subsequently, the lock 160 of the EEPROM 16 is locked again.

In the event that the two initialization codes do not concur, i.en, the inquiry in step 33 is answered in the negative, the path 330 is taken. In a further step 331, either the "clearing" of additional measuring functions is then rejected, or possibly, as an alternative, certain additional measuring functions are "cleared". This "clearing" then takes place as described in the preceding paragraph by means of the path 332 and the steps 333.

In both cases, i.e., if a "clearing" of certain measuring functions takes place as well as if the "clearing" is rejected or takes place only on a trial basis, the user is shown on the display unit 13 in a further step 34 whether or not the upgrading was successful or whether certain measuring functions were cleared on a trial basis.

This exemplary procedure makes it possible to easily upgrade the device without having to send the device to the manufacturer for lengthy periods. The user who would like to upgrade his device only needs to make sure that the right initialization codes are fed to his device. This can take place either in such a way that he orders initialization codes directly from the manufacturer, whereby the respective user is registered and a corresponding invoice can be made out to him. The user can also be left with an initialization code for free, for example, that makes it possible to access on a trial basis an additionally desired measuring function for a predetermined count value. This can take place as is explained below with the help of the flow chart of FIG. 7.

Figure 7:
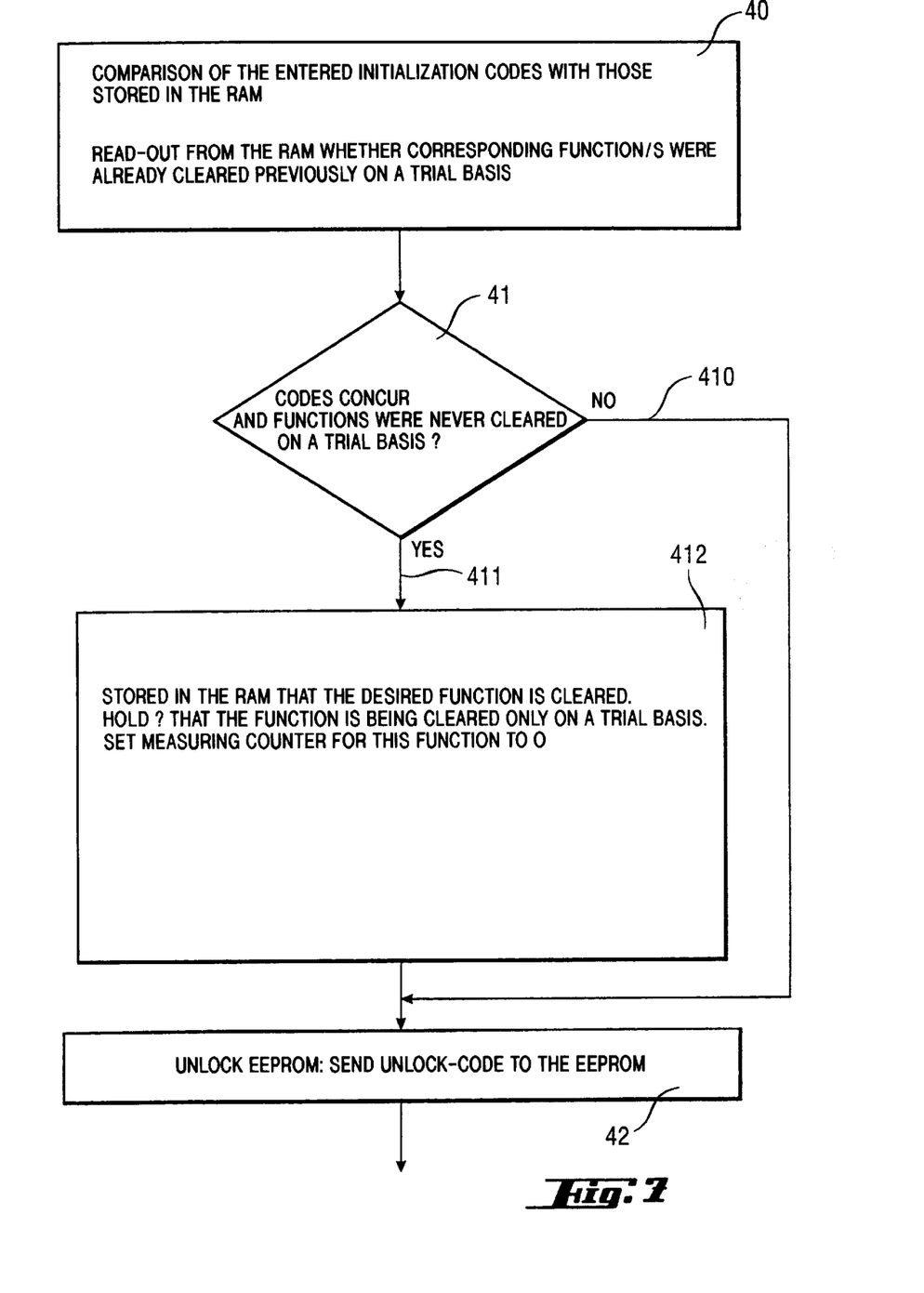
FIG. 7 shows an exemplary flow chart to elucidate steps of an exemplary process for a test initialization of measuring functions.

For this purpose, in a first step 40, an initialization code is fed to the device. The initialization code fed in is compared with the corresponding initialization code that is stored in the RAM 17. In addition, it is read from the RAM 17 whether the desired measuring function was not already cleared previously on a trial basis.

If both inquiries in step 41 are answered in the affirmative, i.e., the initialization codes concur, and if the additional measuring functions were not already "cleared" on a trial basis previously, the path 411 is taken. In a subsequent step 412, it is then stored in the RAM 17 that the additional measuring functions are "cleared". Furthermore, it is established in the RAM 17 that the additional measuring functions are "cleared" on a trial basis (i.e., that by means of a corresponding release code, the measuring function stored in the ROM 15 can be accessed on a trial basis). In addition, a counter for these measuring functions is set at "0". This counter is incremented each time these additional functions are accessed. Furthermore, the lock 160 of the EEPROM 16 is then unlocked, in that the key is sent from the ROM 15 to the lock 160 of the EEPROM 16. In the memory 161 of the EEPROM 16, it is then stored that the additionally desired functions were already cleared previously on a trial basis. Finally, the lock 160 of the EEPROM 16 is locked again.

If only one of the questions in step 41 is answered in the negative, i.e., if either the initialization codes do not concur or the measuring functions desired additionally on a trial basis were already "cleared" on a trial basis previously, the path 410 is taken and the measuring functions desired additionally on a trial basis are not "cleared".

In both cases, i.e., in the case of successful "clearing" on a trial basis as well as in the case of an unsuccessful attempt, the result can be displayed on the display unit 13 in a step 42.

Thus far, an exemplary variant has been discussed in which the user obtains by himself the initialization codes from the manufacturer of the device and/or asks for them from the manufacturer and then feeds the initialization codes to the device himself (e.g., by hand-wheel 120 or via a keyboard). But the upgrading of a device can also take place in such a way that the user brings his device on site to the corresponding representative and the upgrading of the device takes place there. Moreover, the upgrading of the device can take place as explained below with reference to FIG. 8.

Figure 8:
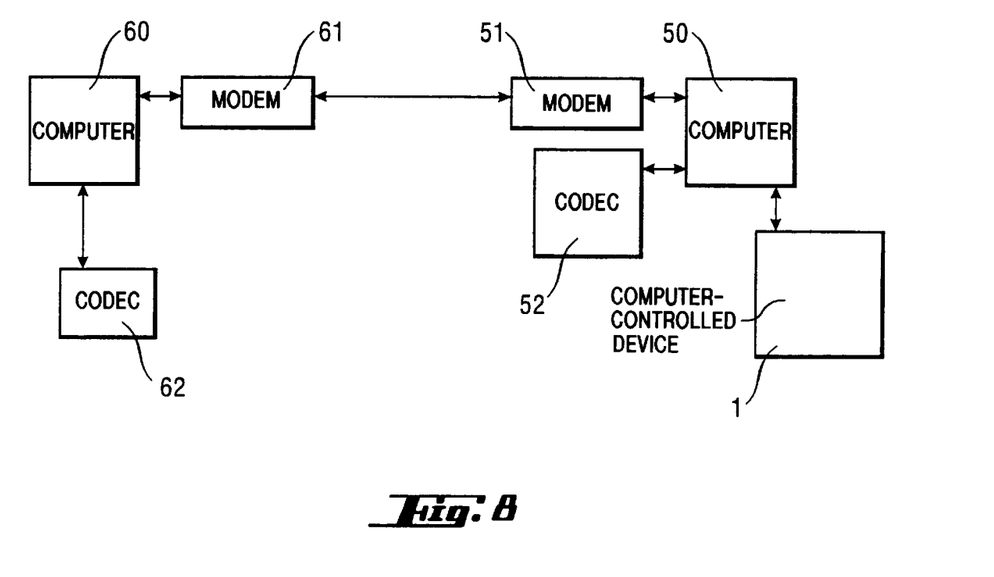
FIG. 8 shows an exemplary embodiment of an initialization of measuring functions via an interface of the device.

In accordance with the FIG. 8 embodiment, the user brings his device on site to the representative and informs the representative what additional measuring functions he would like to execute with his device. The representative on site connects the device via the FIG. 3 interface 18 to a first computer 50 shown in FIG. 8. The first computer 50 is connected via a modem 51 and via another modem 61 with a second computer 60. This second computer 60 is at the device manufacturer's location. All initialization codes, release codes, device codes, etc. for each individual device 1 produced are stored in the memory of this second computer 60. After the first computer 50—and thereby the representative—has identified itself and communicated the device number to the second computer 60, and has explained which additional measuring functions should be executable with the connected device 1, the corresponding initialization codes are called up from the memory of the second computer 60 and transmitted via the modem 61, via a connection line (e.g., a phone line) and the modem 51 to the first computer 50. From there, they are fed via the interface 18 to the device 1, and the measuring functions are initialized in the already explained manner.

Due to the fact that the first computer 50 must first identify itself with the second computer 60 before the corresponding initialization codes are called up from the memory of the second computer 60 and transmitted to the first computer 50, it is also possible to automatically make out an invoice to the representative, since the first computer 50 of the representative is known, after its identification, to the second computer 60 at the device manufacturer's location, and the device manufacturer thus knows to whom he must make out the invoice. On site, the representative then settles accounts with the respective user whose device has been upgraded.

So that the initialization codes cannot be accessed without authorization, the initialization codes that are stored in the memory of the second computer 60 can be transmitted in encoded form. Thus, after the first computer 50 identifies itself to the second computer 60, the initialization codes are first encoded by means of a codec 62 connected with the second computer and transmitted in coded form via the modem 61 and the modem 51 to the first computer 50. As an alternative, the initialization codes can be previously encoded by means of the computer 60. After transmission of the coded initialization codes to the first computer 50, the coded initialization codes are decoded again with the help of another codec 52 connected with the first computer 50 and fed in decoded form via the interface 18 to the device 1.

If anyone should monitor the initialization codes on the transmission path from the second computer 60 to the first computer 50, the only one who can utilize the initialization codes is someone who has, in addition to the corresponding device 1 (recall that the initialization codes are, in an exemplary embodiment, different for each device), also a corresponding codec 52 to decode the initialization codes transmitted in coded form. This increases the security during transmission of the initialization codes.

The variant in which one can upgrade the device 1 in this way can be offered in particular to big customers such as representatives, since the representative must then also have the codec 52 and a corresponding computer 50. In principle, however, it would also be useable for larger private customers or anyone else.

The storage of all initialization codes, all release codes, device codes, etc. at the device manufacturer's location also has the advantage that when, for example, the FIG. 3 EEPROM 16 is defective, the old EEPROM 16 can be reproduced again. If the service technician replaces the EEPROM 16, he can enter via the input unit 12 that no release codes are stored in the RAM 17. The method of procedure already described above then takes place when turning the device on. On the other had, if only the control computer 14 is defective, a new control computer can simplify be installed without further costly measures being necessary in the process. In the same way, the ROM 15, in which basically all measuring functions are always stored, can be replaced with no problem. To be able to use future program versions as well, only the communication protocol with the EEPROM 16 needs to be exactly the same at all times.

As regards the "clearing" on a trial basis of certain measuring functions, it should still be noted that this can take place in the same way as for the definitive "clearing" of certain measuring functions. However, the initialization codes for the "clearing" on a trial basis of measuring functions can also be stored in the ROM 15 and can, in an exemplary embodiment, be the same for all devices in order to simply the managing of the initialization codes for the "clearing" on a trial basis of measuring functions.

It will be appreciated by those skilled in the art that the present invention can be embodied in other specific forms without departing from the spirit or essential character thereof. The presently disclosed embodiments are therefore considered in all respects to be illustrative and not restrictive. The scope of the invention is indicated by the appended claims rather than the foregoing description and all changes which come within the meaning and range of equivalents thereof are intended to be embraced therein.

What is claimed is:

1. Computer-controlled device for detecting optical transmission and/or remittance properties of an object, comprising:

a measuring unit for illuminating the object and for receiving measuring light that has passed through or that has been remitted from the object;

an input unit for selecting a type of measurement of the object, for entering parameters, and for triggering the measurement;

a display unit for displaying values measured;

a first non-volatile memory in which a plurality of measuring functions of the device are stored;

a control unit for controlling all procedures in the device; and a second non-volatile memory for storing respective release codes, each assigned to at least one of said plurality of measuring functions, said release codes being used by said control unit to access the corresponding measuring functions in the first non-volatile memory;

wherein each release code is assigned to a different set of measuring functions, and each set includes at least one of the plurality of measuring functions stored in the first non-volatile memory.

2. Computer-controlled device according to claim 1, wherein all measuring functions executable with the device are stored in the first non-volatile memory, and that in the second non-volatile memory, release codes are stored by which the control unit accesses selected measuring functions of all measuring functions stored in the first non-volatile memory.

3. Computer-controlled device according to claim 1, wherein the second non-volatile memory is an electrically erasable, programmable read only memory (EEPROM).

4. Computer-controlled device according to claim 1, wherein the second non-volatile memory is a lockable memory having contents which can only be accessed by a key code.

5. Computer-controlled device according to claim 4, wherein the contents of the second non-volatile memory can only be accessed by a key code that is unique for each device.

6. Computer-controlled device according to claim 1, further comprising:

a battery-buffered, volatile memory into which the control unit loads the release codes from the second non-volatile memory when the device is initialized.

7. Computer-controlled device according to claim 1, further comprising:

an interface for communication with external devices.

8. Method for operating a computer-controlled device for detecting optical transmission and/or remittance properties of an object comprising the steps of:

illuminating the object and receiving light transmitted through or remitted from the object;

inputting a type of measurement, parameters of measurement, and a signal for triggering the measurement;

displaying measured values;

controlling procedures in the device by accessing at least one of a plurality of measuring functions stored in a first non-volatile memory; and using release codes stored in a second non-volatile memory, each release code corresponding to at least one of the plurality of measuring functions, to access corresponding ones of the plurality of measuring functions stored in the first non-volatile memory;

wherein each release code is assigned to a different set of measuring functions, and each set includes at least one of the plurality of measuring functions stored in the first non-volatile memory.

9. Method according to claim 8, further including a step of:

providing a control unit to call up the release codes from the second non-volatile memory, and with these codes, accessing selected measuring functions stored in the first non-volatile memory.

10. Method according to claim 9, further comprising the steps of:

calling up, via the control unit and release codes which are stored in the second non-volatile memory, selected measuring functions in the first non-volatile memory on a trial basis;

counting each individual trial accessing of the selected measuring functions; and blocking user access to the selected measuring functions after a predetermined number of trial accesses in response to said step of counting.

11. Method according to claim 10, further comprising a step of:

checking each time before a trial accessing of one of said selected measuring functions, whether said one of said selected measuring functions was previously accessed said predetermined number of times, and in this case, blocking said one of said selected measuring functions from being accessed via said control unit on a trial basis again.

12. Method according to claim 8, further comprising the steps of:

checking, when the device is switched on, whether all measuring functions that are accessed with the release codes stored in the second non-volatile memory can be accessed, and if this is not the case, calling up the release codes stored in the second non-volatile memory using the control unit, such that all measuring functions for which release codes are stored in the second non-volatile memory can be accessed from the first non-volatile memory.

13. Method according to claim 8, wherein the release codes are locked in the second non-volatile memory, and can only be accessed with a key code.

14. Method according to claim 13, wherein the release codes locked in the second non-volatile memory can only be accessed by a key code that is unique for each device.

15. Method for initializing measuring functions of a computer-controlled device for detecting optical transmission and/or remittance properties of a measuring object, comprising the steps of:

accessing measuring functions stored in a first non-volatile memory using a control unit;

feeding a device-specific initialization code to open a second non-volatile memory;

storing release codes in said second non-volatile memory; and accessing said measuring functions stored in the first non-volatile memory by the control unit during operation of the device using corresponding release codes stored in the second non-volatile memory;

wherein each release code is assigned to a different set of measuring functions, and each set includes at least one of the measuring functions stored in the first non-volatile memory.

16. Method according to claim 15, wherein the initialization code is input manually via an input unit.

17. Method according to claim 15, wherein the initialization code is input via an interface for communication with an external device.

18. Method according to claim 17, wherein the computer-controlled device is connected via the interface with a first computer, said first computer being connected to a second computer having a non-volatile memory in which all initialization codes for each individual device are stored, said method further including the steps of:

transferring, after an identity of the first computer is established, a desired initialization code from the non-volatile memory of the second computer via the first computer and the interface, to the computer-controlled device to thereby open the second non-volatile memory and supply release codes for use by said computer controlled device.

19. Method according to claim 18, further comprising the steps of:

encoding the initialization code before the transmission of the initialization code from the second computer to the first computer; and decoding the initialization code after the transmission, before the initialization code is fed via the interface to the computer-controlled device.

20. Method according to claim 15, further comprising the step of:

feeding to the computer controlled device an initialization code by which release codes are stored in the second non-volatile memory of the device.

21. Method according to claim 15, further comprising the step of:

feeding to the computer-controlled device an initialization code by which release codes are stored in the second non-volatile memory, said release codes being used by said control unit to access selected measuring functions in the first non-volatile memory on a trial basis, during which each individual trial accessing of the selected measuring functions is counted and after a predetermined number of trial accesses, said selected measuring functions are blocked from access by the control unit.

* * * * *